United States Patent [19]

Belanger et al.

[11] 4,293,399

[45] Oct. 6, 1981

[54] DEVICE FOR DETECTING AND MEASURING THE CONCENTRATION OF GASEOUS HYDROGEN DISSOLVED IN A FLUID

[75] Inventors: Guy Belanger; Gilles Missout, both of Quebec, Canada

[73] Assignee: Hydro-Quebec, Montreal, Canada

[21] Appl. No.: 141,048

[22] Filed: Apr. 17, 1980

[30] Foreign Application Priority Data

Jun. 22, 1979 [CA] Canada .................................. 330653

[51] Int. Cl.³ ...................... G01N 27/28; G01N 27/46
[52] U.S. Cl. ................................................. 204/195 P
[58] Field of Search ............................ 204/195 P, 1 T

[56] References Cited

U.S. PATENT DOCUMENTS 4,233,143  11/1980  Knudsen ......................... 204/195 P

FOREIGN PATENT DOCUMENTS 1054223  5/1979  Canada ................................ 204/1 T Primary Examiner—G. L. Kaplan
Attorney, Agent, or Firm—Schwartz, Jeffery, Schwaab, Mack, Blumenthal & Koch

[57] ABSTRACT

Discloses is an improved device to facilitate detecting and measuring the concentration of gaseous hydrogen dissolved in a fluid. A polymeric membrane is in contact with the fluid and permeable to the hydrogen gas. An electrolyte is provided which is capable of producing oxidation of the hydrogen diffused through the membrane at a first electrode, and reduction of an oxygen-containing gas such as air, at a second electrode. The connection of a measuring device across the electrodes measures the intensity of the current generated by the electrochemical reaction of oxidation of the hydrogen gas. The electrodes and the electrolyte are mounted in an electrode mounting unit which includes a first, tightly sealed enclosure encased within a second, tightly sealed enclosure. The mounting unit is tightly mounted into a hollow housing. This housing is fixed to a base across one extremity of which extends the polymeric membrane.

10 Claims, 5 Drawing Figures

DEVICE FOR DETECTING AND MEASURING THE CONCENTRATION OF GASEOUS HYDROGEN DISSOLVED IN A FLUID

BACKGROUND OF THE INVENTION

The present invention relates generally to an improved device for detecting and measuring the concentration of gaseous hydrogen dissolved in a fluid.

More especially, this invention relates to an improved detecting and measuring device in which the concentration of gaseous hydrogen dissolved in a fluid is determined by the measure of an electric current generated by electro-chemical oxidation of the gaseous hydrogen at an electrode of detection.

A device of the above-mentioned type is already known and forms the subject matter of Canadian Pat. No. 1,054,223 issued on May 8, 1979 in the name of HYDRO QUEBEC. The detecting and measuring device disclosed in this patent comprises; a polymeric membrane permeable to hydrogen gas in contact with the fluid; an electrolyte capable of producing oxidation of the hydrogen gas diffused through the polymeric membrane at a first electrode and reduction of an oxygen-containing gas, such as air, at a second electrode; a measuring device connected across the electrodes for measuring the intensity of the electrical current generated by the electrochemical reaction of oxidation of the hydrogen gas, this intensity being proportional to the concentration of hydrogen in the fluid.

This already known device is essentially to provide an accurate diagnosis of the incorrect operation of transformer, a circuit breaker, a reactance or any electrical apparatus using a dielectric liquid as insulating substance. It is indeed well known that, in the event of a disturbance or malfunction of one of the abovementioned apparatus due to a too high working temperature or a high electrical discharge, there is production of hydrogen gas in the insulating liquid. Accordingly, it can be easily understood that the utilization of a device allowing for immediate detection of an increase of the concentration of gaseous hydrogen dissolved in the insulating liquid, is advantageous since it allows immediate diagnosis of the incorrect operation of the electrical apparatus on which the device is mounted, and, when this incorrect operation is timely located, to avoid irrepairable ruin of the apparatus.

The various experiments that were carried out by the applicant on the device disclosed in the above-mentioned Canadian Patent, have shown however that while the basic concept is valid, the various practical embodiments disclosed in the above Canadian patent have drawbacks when they are used for a relatively long period of time in certain regions. These would be those regions where the climatic conditions are extremely hard, or where they would be very difficult to reach and thus require utilization of very reliable devices. These experiments showed that the various embodiments disclosed in the above-mentioned Canadian patent were often subject to leak, particularly of electrolyte, making the device inoperative. These experiments also showed that these various embodiments as a unit were cumbersome, since it is necessary to remove practically all the internal elements of the device one by one in order to reach one of these elements or to introduce or change the electrolyte. These experiments further showed that in the regions subject to high variations of temperature, such as, for example, The Canadian Far North, the measurements obtained were very unsteady and very difficult to follow and read.

SUMMARY OF THE INVENTION

An object of the present invention is to provide an improved device of the above-mentioned type, which overcomes the drawbacks previously mentioned.

A further object of the present invention is to provide a device which has an excellent water-tightness and can be very easily dismantled into several modules which can be easily and independently disassembled if needed.

A still further object of the present invention is also to provide an improved device of the above-mentioned type, to which is connected a system for controlling the temperature and thus automatically compensating for variations in the signals transmitted by the electrodes in regions subject to temperature fluctuations.

The above and other objects are achieved in the present invention by providing three separate modules, a base, a hollow housing, and a mounting device for the electrodes. The base and the hollow housing are attached to the receptacle containing the fluid whose hydrogen content is to be monitored. The base contains a channel therethrough and is connected to a similar channel in the hollow housing. Placed between the base and the hollow housing is the requisite polymeric membrane. Thus, by separating the hollow housing and the base, ready access is provided to polymeric membrane. The electrodes and electrolyte are provided in a mounting unit which is removably insertable in the hollow housing. Thus, it can be independently removed for maintenance without disturbing the polymeric membrane. This mounting unit includes a bucket-shaped container the top of which is closable by means of a cap. Three individual holding elements are inserted into the container and all elements have a central aperture therethrough. A first electrode is mounted between first and third holding elements and a second electrode is mounted between second and third holding elements, such that the two electrodes define a space in the central channel. This space is filled with electrolyte and one end of the space is in fluid communication with the polymeric membrane and the other end in communication with an oxygen-containing gas. Thus, the passage of hydrogen through the polymeric membrane will cause oxidation of the hydrogen at the first electrode and reduction of oxygen at the second electrode generating a signal therebetween which is indicative of the hydrogen concentration in said fluid.

BRIEF DESCRIPTION OF THE DRAWINGS

A more complete appreciation of the invention and the attendant advantages thereof will be more clearly understood by reference to the following drawings, wherein.

DETAILED DESCRIPTION OF PREFERRED EMBODIMENTS

Figure 1:
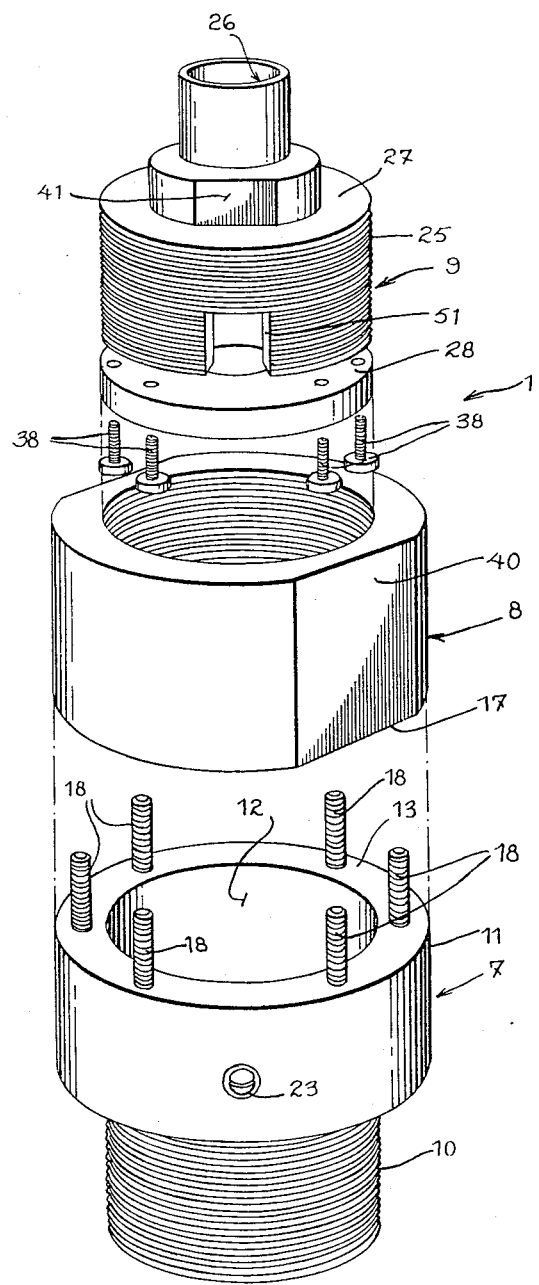
FIG. 1 is an exploded, perspective view of one embodiment of the present invention.

The improved device according to the invention, which is of the above-mentioned type and is meant for being fixed into an aperture provided in one of the walls of a receptacle containing a fluid, is characterized in that it comprises:

a base fixable into the aperture provided in the one wall of the receptacle, this base being provided with a central channel through which the fluid may pass;

a bucket-shaped hollow housing having a bottom with an opening pierced therein, this housing being tightly fixed onto the base in such a manner that the central channel of the base is facing the opening of the housing and the polymeric membrane is intercalated and held between the central channel of the base and the opening of the housing; and a unit for mounting the electrodes and the electrolyte, which unit is inserted within and fixed to the hollow housing.

In accordance with the invention, the mounting unit comprises:

a hollow, bucket-shaped container having a bottom with a small opening pierced therein, this container being so shaped as to be insertable into the hollow housing;

a cap with a small, central opening pierced therein, this cap being designed for being fixed onto the container;

a first, bucket-shaped holding element having a bottom with a small opening pierced therein, this first holding element being so shaped as to be insertable into the container;

a second, cap-shaped holding element having a small, central opening pierced therein, for tightly closing the first holding element; and a third holding element with a central channel pierced therein, this third holding element being so shaped as to be insertable within the first holding element and held therein owing to the second holding element.

The container, the cap and the first, second and third holding elements are positioned in such a manner that their respective openings and central channel are aligned with respect to each other.

The first electrode is inserted and held between the bottom of the first, bucket-shaped holding element and the third holding element, across the central channel of this third holding element. The second electrode is inserted and held between the third holding element and the second, cap-shaped holding element, across the small opening of this second holding element. The electrolyte is contained within the central channel of the third holding element.

After having inserted the electrodes, the first, second and third holding elements are inserted within the container and securely held together therein in a tight manner by fixation of the cap over the container, the container and its cap being in turn inserted and fixed into the hollow housing.

Thus, the improved device according to the invention includes an electrode mounting unit comprising a first, tightly sealed enclosure encased with a second, tightly sealed enclosure. This mounting unit forms a first module which can be fixed within the hollow housing forming a second module. This hollow housing is then tightly fixed onto the base which forms a third module. As can be understood, each module can be easily removed and disassembled if necessary.

In accordance with a preferred embodiment of the invention, a thermistor is inserted between the container and the cap of the holding unit. This thermistor is connected to a multifunction converter mounted between the measuring device and the electrodes. This converter permits compensation for the variations of the intensity of the current generated between the electrodes according to the fluctuations of temperature of the device as measured by the thermistor.

According to another preferred embodiment of the invention, the improved device is located within an insulated, thermostated and tight enclosure.

The two above-mentioned preferred embodiments of the invention are particularly advantageous since they allow correct interpretation of the data given by the measuring device independently of the climatic conditions.

Figure 2:
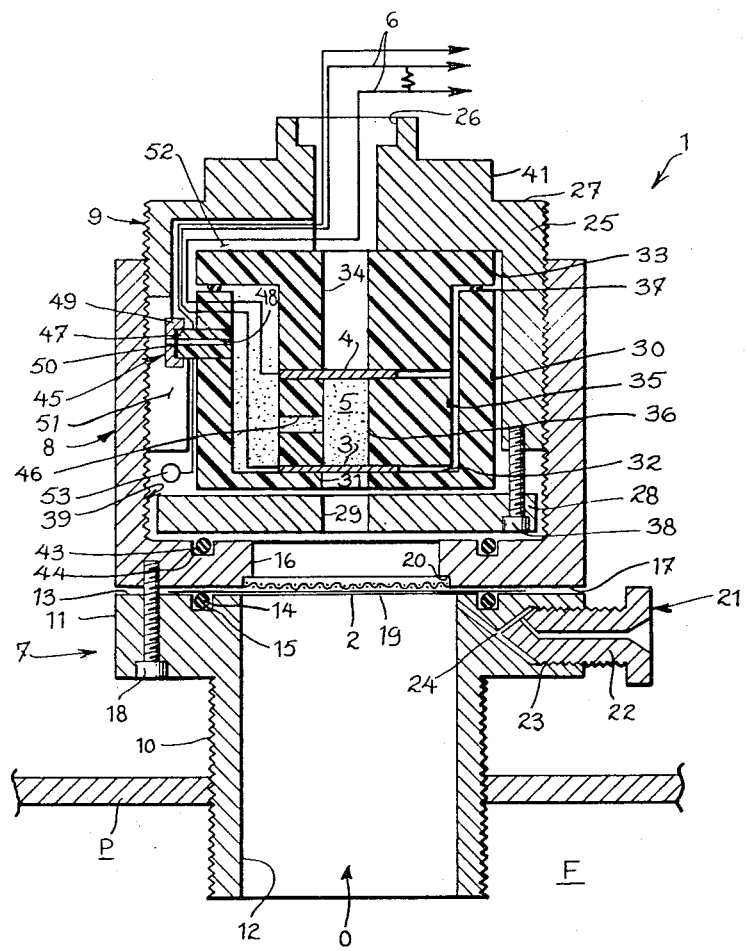
FIG. 2 is a longitudinal, cross-sectional view of the device shown in FIG. 1.

Referring now to the drawings wherein like reference characters designate like parts throughout the several views, the device 1 shown in FIGS. 1 and 2 is used for detecting and measuring the concentration of gaseous hydrogen dissolved in a fluid F contained in a receptacle provided with a wall P, said device having an aperture 0 to bring the fluid F into contact with the detecting device.

The basic elements of the detecting device 1 consist of a polymeric membrane 2 which is permeable to hydrogen, a detection electrode 3 at which occurs the oxidation of the hydrogen diffused through the pores of the polymeric membrane 2, an electrode 4 in contact with an oxygen-containing gas such as air and at which occurs the reduction of the oxygen contained in that gas, and an electrolyte 5 in contact with both electrodes 3 and 4 and so selected as to carry out the desired oxido-reduction reactions at both electrodes.

It will be only reminded here that the electrodes 3 and 4 of the device 1 are connected by means of wires 6 to a measuring device (not shown) which permits one to measure the intensity of the current generated by the oxido-reduction reactions occurring at the electrodes.

In fact, a major improvement of the improved detecting device lies in the structure and the arrangement of its various constituting elements which are used for maintaining the above-mentioned basic elements in cooperative relationship.

These various constituting elements form together three distinct substructures which can be listed as follows: a base 7; a hollow housing 8; and a mounting unit 9 for the electrodes and the electrolyte.

The base 7 and the housing 8 are designed for being fixed into the aperture 0 provided in the wall P of the receptacle containing the fluid F, to hold the whole device and to allow the fluid F to reach the polymeric membrane 2. The base 7 comprises two sections 10 and 11 which are preferably cylindrical and extend coaxially each other. Section 10 is especially designed for being screwed or welded into the aperture provided in the wall P. The base 7 includes a central channel 12 extending through its entire length to allow fluid F to come into contact with the polymeric membrane 2 which bears against the external surface 13 of section 11 and extends across the channel 12.

To prevent leaks of the fluid F out of the detecting device 1, an O-ring seal 14 is inserted between the membrane 2 and the external surface 13 of section 11 of the base. This seal 14 can be inserted in a groove 15 machined for this purpose in the surface 13, as shown in FIG. 2.

The hollow housing 8 is designed for being fixed in a removable manner onto the base 7 and for protecting the mounting unit 9 used for maintaining the electrodes and the electrolyte. This hollow housing 8 is in the shape of a large bucket and is provided with an opening 16 in its bottom 17. This bottom which is preferably circular and has substantially the same surface area as the external surface 13 of the base 7, is used for fixing hollow housing 8 in a removable manner on the base 7 by means of a set of bolts 18 located all around the periphery of section 11 of the base. The bolts 18 pass through this section 11 and are screwed into corresponding threaded holes located all around the bottom 17 of the hollow housing 8 and extending in a direction parallel to the axis of the base.

The opening 16 provided in the bottom of the hollow housing 8 is located so as to face the central channel 12 of the base when the hollow housing is fixed onto this base.

The hollow housing 8 is used not only for receiving the mounting unit 9 but also for maintaining the polymeric membrane 2 across the central channel 12 of the base. In fact, the polymeric membrane 2 is inserted between the external surface 13 of the base and the bottom 17 of the hollow housing and is held solidly therebetween in a tight manner when the bolts 18 are screwed. The O-ring seal 14 prevents leaks between the membrane and surface 13 when the base and hollow housing are bolted together.

A grid 19 is located in a recess 20 machined in the bottom 17 of the hollow housing 8, just behind the membrane 2. This grid 19 essentially serves to reinforce and protect the polymeric membrane 2, particularly against the over pressure of the fluid F.

To allow easy taking of samples of fluid F just before the polymeric membrane 2 for the purpose of analysis, a sample collector 21 can be provided onto the base 7. This collector 21 comprises a rotatable valve 22 inserted into a threaded opening 23 communicating with the central channel 12 of the base 7 owing to a small connecting channel 24. This collector advantageously allows for direct taking of samples of the fluid without having to dismantle the detecting device 1 or to open the apparatus to which the device is fixed.

As mentioned above, the hollow housing 8 receives the unit 9 used for mounting the electrodes and holding the electrolyte.

This mounting unit 9 comprises five elements which are as follows:

a bucket-shaped, hollow container 25 insertable into hollow housing 8 having a small opening 26 pierced into its top 27;

a cap 28 for covering container 25 having a small opening 29 pierced in its middle;

a first, bucket-shaped holding element 30 insertable into container 25 having a small opening 31 pierced in its bottom 32;

a second, cap-shaped holding element 33 having a small opening 34 pierced in its middle, for closing in a tight manner the first holding element 30; and a third holding element 35 with a central channel 36 passing therethrough, this third holding element being shaped as so to be insertable into the first holding element 30 and to be held therein owing to the second holding element 33.

As can be seen on FIG. 2, the first, second and third holding elements 30, 33 and 35 serve to hold the electrodes 3 and 4 and the electrolyte 5. On the other hand, the hollow container 25 and the cap 28 serve to securely hold the three holding elements 30, 33 and 35 together and to permit the mounting of the unit within the hollow housing 8 in such a manner that the small openings 26, 29, 31 and 34 and the central channel 36 of the five elements of the mounting unit 9 are aligned and form together a channel opening at one end to the atmosphere and at the other end to the opening 16 provided in the bottom of the hollow housing 8.

As can also be seen in FIG. 2, the electrode 3 is inserted and held between the bottom 32 of the first holding element 30 and the third holding element 35 across the central channel 36 of this third holding element. The oxidation of the gaseous hydrogen occurs at electrode 3 after diffusing through the polymeric membrane 2 and passing through openings 16, 29 and 31.

The other electrode 4 is inserted and held between the third holding element 35 and the second holding element 33 which also serves as a cap for the first holding element 30. This electrode 4 extends across the small opening 34 of the second holding 33 and thus is in direct contact with the air via the small opening 26 in the bottom 27 of the container 25.

The elements 30, 33 and 35 are in permanent contact with the electrodes and the electrolyte and accordingly must be made of an insulating material which is inert and resistant to the electrolyte. As suitable insulating material for these holding elements, use can be made, for example, of polypropylene.

The base 7, the hollow housing 8, the container 25 and the cap 28 can be made of any kind of material sufficiently resistant to protect the device. This material can be, for example, brass.

As indicated above, the first, second and third holding elements 30, 33 and 35 are securely held together in a tight manner. This tightness is obtained not only owing to the particular shape of the first holding 30 but also by means of O-ring seal 37 inserted between the upper edge of the first holding element 30 and the bottom surface of the second holding element 33 in contact with this first holding element.

The first, second and third holding elements 30, 33 and 35 are all together inserted into the container 25 in such a manner that the second holding element 33 be in contact with the bottom 27 of this container. The holding elements 30, 33 and 35 are securely held within the container 25 by fixation of the cap 28 on this container.

The cap 28 is fixed onto the container by means of bolts 38. These bolts pass through the cap all around its periphery in a direction parallel to the axis of the small opening 29, and they are screwed into corresponding threaded holes provided for this purpose in the upper edge of the lateral walls of container 25.

The mounting unit 9 composed of the first, second and third holding elements 30, 33 and 35 securely encased between the container 25 and the cap 28, is inserted in turn and fixed into the hollow housing 8 in such a manner that the surface of the cap 28 is in contact with the surface of the bottom 17 of the housing.

To allow this insertion, the container 25 and its cap 28 are so shaped as to have a surface equal to or slightly smaller than the internal surface of the hollow housing 8.

The mounting unit 9 can be fixed into the hollow housing in any conventional manner. However, when the container and the hollow housing are cylindrical, use is preferably made of threads 39 provided on the internal and external walls of the container and hollow housing, respectively. Thus, the mounting unit 9 can be screwed into the hollow housing 8 until the cap 28 is in contact with the internal surface to the bottom 17 of the housing. To facilitate screwing, cut-off portions 40 and 41 can be made on the respective surfaces of the hollow housing 8 and the container 25 to permit the utilization of a wrench.

To ensure suitable tightness between the mounting unit 9 and the bottom of the hollow housing 8, an O-ring seal 43 is located in the bottom of the hollow housing. This seal may be held in a groove 44 machined into the internal surface of the bottom 17 of the hollow housing.

One of the main advantages of the above described detecting device 1 lies in that the base 7, the hollow housing 8 and the mounting means 9 can be easily separated from each other without dismantling the whole device, this being particularly interesting when one wants to check or repair only one element of the device and does not want to completely dismantle the other elements.

Another advantage of the above-described detective device 1 lies in a mounting unit comprising a first, tightly sealed enclosure constituted by the first, second and third holding elements, which enclosure is encased within a second, tightly sealed enclosure constituted by the container and its cap. This particular arrangement which is obtained owing to the bucket-shape of the first holding element 30 and container 25, substantially reduces the risk of leaks.

In order to facilitate the maintenance of the detecting device 1, a plug 45 is located in the lateral wall of the first holding element 30 to permit filling of the central channel 36 of the third holding element 35 with electrolyte via a lateral channel 46 provided for this purpose in the third holding element. This plug 45 comprises a first section 47 provided with a channel 48 to allow the air to escape during screwing after filling. This section 47 is closed by a second, cap-shaped pierced section 49 the bottom of which is provided with a small gas permeable membrane so used for closing the channel 48.

The plug 47 is easily accessible without having to dismantle the mounting unit 9 owing to a recess 51 machined into the lateral wall of the container 25 in which are encased the first, second and third holding elements. This recess 51 permits one to easily reach the plug and thus to check the level of the electrolyte and eventually to fill up the channel of the third holding element 35.

As already mentioned above, the electrodes 3 and 4 of the device 1 are connected to a measuring instrument by means of two wires 6. These wires 6 pass in a tight manner through the wall of the first holding element 30 and exit from the mounting unit 9 via a recess 52 in the container 25. This recess 52 opens into the small opening 26.

The above-described, improved detecting device, works in a similar manner as the device disclosed in the Canadian Patent No. 1,054,223 already mentioned in the Background of the present disclosure. However, this improved device 1 can be advantageously completed by an electronic circuit allowing control of its functioning and taking into account the variations of the external temperature which can substantially affect the measured data.

Any suitable electrolyte can be used as long as it will enable the electrochemical oxidation of hydrogen at the electrode closest to the polymeric membrane and the reduction of oxygen at the other electrode. A number of electrolytes are known for this purpose and include electrolytes constituted by an acid, such as phosphoric, sulfuric or perchloric acids, by an alkali solution such as the potassium and sodium hydroxides, or even a solid electrolyte formed within an ion exchanging membrane.

Figure 3:
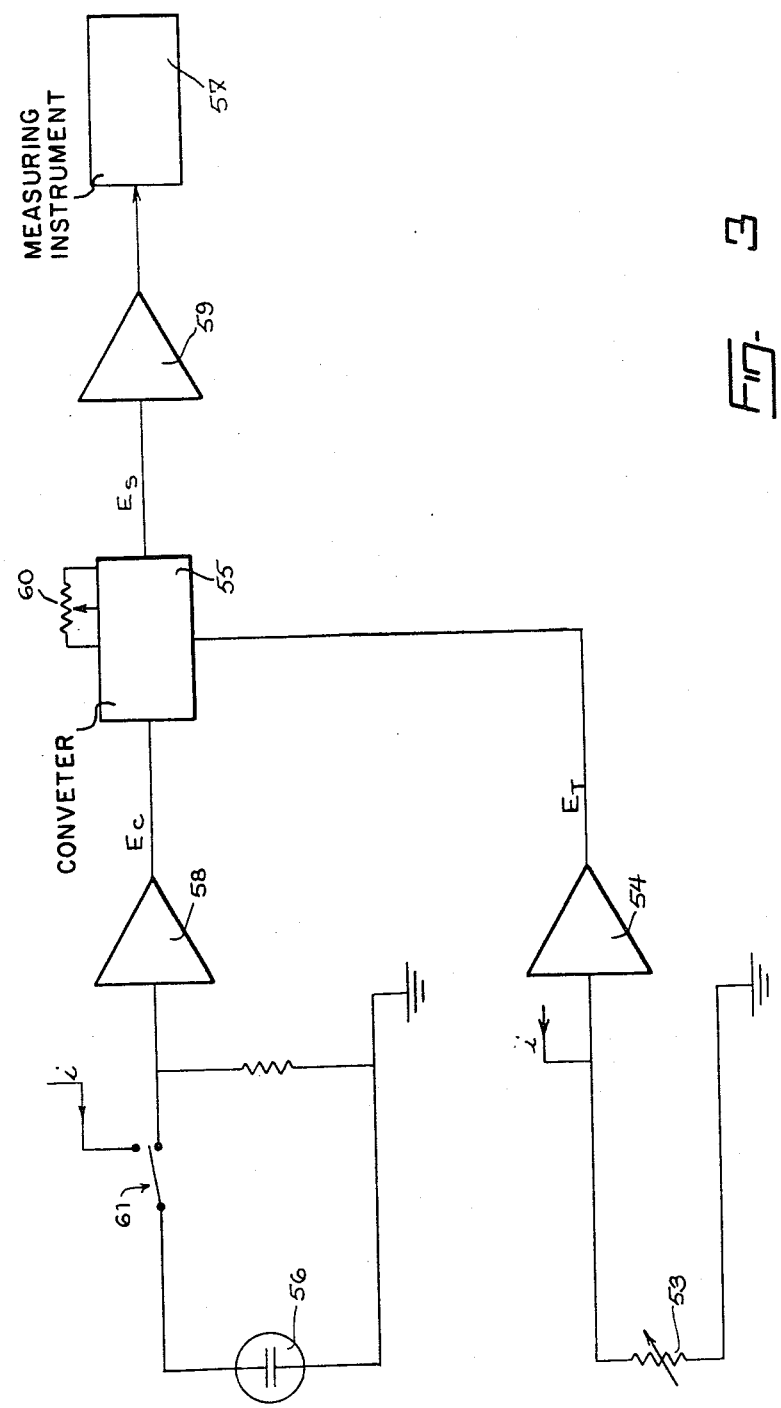
FIG. 3 is a schematic diagram of an electronic control circuit usable in combination with the device shown in FIGS. 1 and 2.

This electronic circuit of control and correction is illustrated in a schematic manner on FIG. 3. This circuit includes a thermistor 53 located into the hollow housing 8 as shown in FIG. 2, between the container 25 and the cap 28 of the mounting unit 9. This termistor 53 is connected to an amplifier 54 by a wire passing through the same recess 52 as wires 6 of the electrodes 3 and 4. The amplifier 54 amplifies the signal received from the thermistor and transmits the amplified signal $E_T$ to a multifunction converter 55 connected in series between the cell 56 constituted by the two electrodes 3 and 4 and the electrolyte 5, and the measuring instrument 57.

More especially, the multifunction converter 55 is mounted in series between a first amplifier 58 which is connected to the cell 56 for amplifying the signal from this cell, and a second amplifier 59 mounted just before the measuring instrument 57. The multifunction converter 55 is suitably calibrated to process the signal $E_C$ transmitted by the first amplifier 58 so as to take into account the fluctuation of temperature of the device 1 as measured by the thermistor 53.

The output signal $E_S$ fed to the second amplifier 59 located behind the multifunction converter is given by the formula:

$$E_S = E_C/E_T^m$$

in which m is a constant of the converter 55, which is adjustable by means of a potentiometer 60.

The signal $E_C$ from the cell 56 corresponds to the following formula:

$$E_C = k[C]e^{B/T}$$

in which k and B are constants of the cell;

C is the concentration of gaseous hydrogen dissolved into the fluid; and

T is the temperature of the cell expressed in degree Kelvin.

The signal $E_T$ from the thermistor corresponds to the following formula:

$$E_T = k'e^{B'/T}$$

in which k' and B' are constants from the thermistor and T is the temperature of the cell expressed in degree Kelvin.

By suitably choosing the constant m appearing in the formula of the output signal $E_S$ by adjusting the potentiometer 60, it is possible to eliminate the exponential factors appearing in the formula of the signal $E_S$. The signal $E_S$ thus becomes independent of the temperature and directly proportional to the concentration of the gaseous hydrogen dissolved in the fluid.

To allow calibration of the multifunction converter and to control the operation of the improved device 1 a relay 61 can be provided between the cell 56 and the first amplifier 58. When this relay is operated, it supplies a constant current i generated by a diode to the cell for a given interval of time. The introduction of this current into the cell produces electrolysis of water and formation of gaseous hydrogen. By switching-off the current i, this gaseous hydrogen generated by electrolysis operates the cell 56 for a few seconds and thus allows the operator to verify whether or not the device 1 works adequately. If this is not the case, it is then necessary to check the device and particularly the presence of electrolyte between the electrodes.

The control circuit can also be used for adjusting the converter. For this purpose, a constant concentration of gaseous hydrogen is used and a first output signal $E_S{}^o$ is measured for a temperature $T^o$. A second output signal $E_S{}^1$ is then measured for a temperature $T^1$ different from $T^o$. Lastly, the potentiometer 60 is adjusted so that $E_S{}^o$ be equal to $E_S{}^1$ although the temperatures $T^o$ and $T^1$ are different.

Therefore, as can now be understood, this electronic circuit is particularly advantageous since it allows correct interpretation of the data given by the measuring instrument under any climatic condition.

The above-described device 1 illustrates a first embodiment of the invention. However, it is possible to conceive other embodiments of the invention, such as the improved device 101 shown in FIG. 4.

Figure 4:
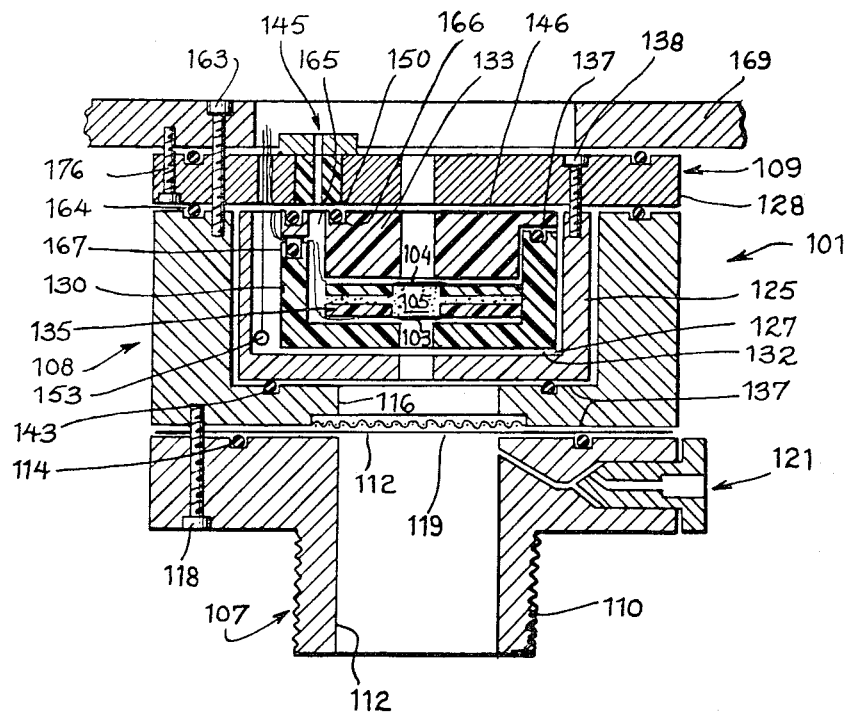
FIG. 4 is a longitudinal, cross-sectional view of a second embodiment of the present invention.

For the purpose of simplification, the various elements of the device 101 shown in FIG. 4 have been identified by the same numeral references as the elements of the above-described device 1, except that they have been increased by 100.

A main difference existing between the improved device 101 and the above-described device 1 lies in the manner of inserting and mounting the mounting unit into the hollow housing.

In the improved device 101, the first, second and third holding elements 130, 133 and 135 are inserted into the container 125 in such a manner that the bottom 132 of the first, bucket-shaped element is in contact with the bottom 127 of the container. When so encased, the mounting unit 109 is inserted into the hollow housing 108 in such a manner that the bottom of the container 127 is in contact with the bottom 137 of the bucket-shaped hollow housing 108. This mounting unit 109 is fixed in a tight manner against the bottom of the hollow housing 108 by means of bolts 163 through the periphery of the cap 128 the surface of which bears against the upper edges of the lateral wall of hollow housing 128, with an O-ring seal 164 interposed therebetween.

As in device 1, the third holding element 135 of the device 101 is provided with a lateral channel 146 to allow filling of its central chamber with electrolyte 105.

This filling is facilitated by a plug 145 advantageously located in the cap 128 of the mounting unit 109. This particular arrangement allows the filling of the lateral and central channels of the third holding element 135 via a conduit provided for this purpose in the second holding element 133, without having to dismantle the device 101 nor the mounting unit 109. In this case, a gas permeable membrane 150 is located at the surface of the second holding element 133 and is tightly held thereon by means of an O-ring seal 166.

It must be noted in this second embodiment that the wires 106 connecting the electrodes 103 and 104 to the measuring instrument tightly exit from the first holding element 130 owing to a seal 167 suitably located in the lateral wall of this first holding element. To complete tightness, use is made of lamellae of platinum as conducting wires, which can be more easily sealed by the seal 167.

The improved device 101 is fixed by section 110 of its base 107 to an aperture O providing for this purpose in the wall of a receptacle containing the fluid F in which the concentration of gaseous hydrogen dissolved is to be measured.

Figure 5:
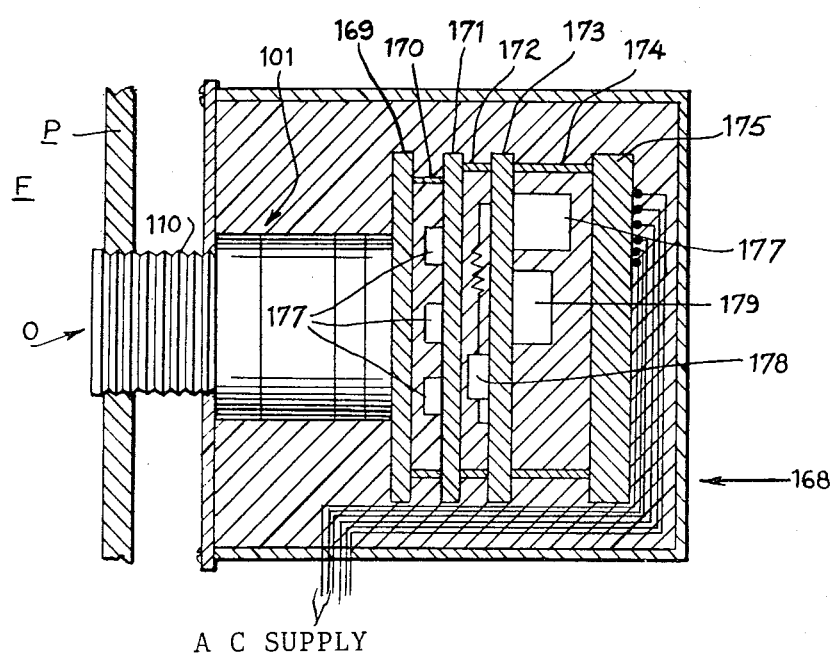
FIG. 5 is a cross-sectional view of the device shown in FIG. 4 located in a thermostated enclosure.

To ensure complete autonomy to the device 101, the same can be located in an enclosure 168 which is thermally insulated and is water-proof (see FIG. 5).

This insulated enclosure 168 is designed to receive a complete electronic circuit allowing for processing of the signals from the device 101. This electronic circuit is preferably mounted on several plates 169, 171, 173 and 175 held parallel to each other at given intervals by means of braces 170, 172 and 174. The first plate 169 is fixed onto the device 101 by a set of bolts 176. Of course, other methods of fixation can be used. However, the system of mounting shown in FIG. 4 is particularly advantageous since it allows for a dismantling of the electronic circuit and the mounting unit in a single operation, by merely unscrewing of the bolts.

The first plate 169 serves as support for the second plate 171 onto which is fixed an electronic circuit of control and correction 177 similar to the one diagrammatically illustrated in FIG. 3. The third plate 173 fixed onto the second plate 171 by the braces 172 serves to fix a heating system associated with a thermistor to maintain the electronic circuit mounted onto the second plate at a constant temperature. The third plate also serves to support the power supplying circuit 179 of the electronic circuit.

The fourth plate 175 fixed to the third plate by the braces 174 serves to support the contacts necessary for operating the device 101 from the outside of the enclosure 168. As can be easily understood, there are six contacts which are as follows: two output wires for transmitting the signals measured, two intput wires to allow verification and calibration of the circuit, and two wires for AC power for the electronics.

Although the invention has been described relative to specific embodiments thereof, it is not so limited and many modifications and variations thereof will be readily apparent to those skilled in the art in light of the above teachings. It is, therefore, to be understood, that within the scope of the appended claims, the invention may be practiced otherwise than as specifically described.

The embodiments of the invention in which an exclusive property or privilege is claimed are defined as follows:

What is claimed is:

1. A device for detecting and measuring the concentration of gaseous hydrogen dissolved in a fluid, said fluid contained in a receptacle having a wall, said wall including means defining an aperture therein, said device providing an electrical signal indicative of said concentration, said device comprising:

means for providing a base, said base including a central channel therein;

means for sealingly mounting said base on said wall, said central channel of said base in fluid communication with said aperture and said fluid in said receptacle;

a polymeric membrane in contact with said fluid and permeable to hydrogen gas, said membrane covering said central channel;

means for defining a bucket-shaped, hollow housing having a bottom, said housing including means defining an aperture in said bottom;

means for sealingly mounting said housing on said base with said polymeric membrane mounted between said housing and said base, said membrane preventing the passage of fluid and permitting the passage of hydrogen gas from said channel to and through said aperture in said hollow housing;

first and second electrodes;

means, insertable in said hollow housing, for mounting said electrodes and defining a space therebetween, said means mounting said first electrode adjacent said aperture in said hollow housing;

means defining an electrolyte, disposed at least in said space between said electrodes, capable of producing oxidation of said hydrogen gas at said first electrode and reduction of an oxygen-containing gas at said second electrode;

said electrode mounting means comprising:

a hollow, bucket-shaped container, insertable into said hollow housing, having a bottom, said container including means defining an opening in said container bottom;

means defining a cap for removably closing said container, said cap including means defining an opening therein;

a first, bucket-shaped holding element, insertable in said container, said element having a bottom, said element including means defining an opening in said element bottom;

a second, cap-shaped holding element, insertable in said container, said second holding element including means defining an opening therein, said second holding element for tightly closing said first holding element;

a third holding element, insertable in said first holding element and held by said second holding element, said third holding element including means defining a central channel therein;

means for removably mounting said cap on said container, said first electrode removably mounted between said first and third holding elements and said second electrode removably mounted between said second and third holding elements, said openings in said cap and said first holding element, said central channel in said third holding element, and said openings in said second holding element and said container combine to define a central channel disposed in said electrode mounting means with said gap opening adjacent said aperture in said hollow housing at one end and said container opening in gaseous communication with said oxygen-containing gas, said cap, container and means for removably mounting said cap on said container combining to securely sandwich said holding elements and electrodes between said cap and container, said space between said electrodes defined by said central channel in said third holding element; and means for removably fixing said electrode mounting means in said hollow housing.

2. A detecting device according to claim 1, wherein said means for sealingly mounting said hollow housing on said base comprises a plurality of bolts;

means for reinforcing said membrane, said reinforcing means comprising a grid located adjacent said membrane, said grid extending across said central channel behind said polymeric membrane; and a first O-ring seal located between said base and said hollow housing;

said means for removably fixing said electrode mounting means in said hollow housing including a second O-ring seal located between said electrode mounting means and the bottom of said hollow housing.

3. A detecting device according to claim 2, wherein said means for removably mounting said cap on said container comprises a plurality of bolts around the periphery of said cap, each of said bolts extending in a direction parallel to a longitudinal axis of said central channel in said electrode mounting means.

4. A detecting device according to claim 3, wherein said means for removably fixing said electrode mounting means in said hollow housing comprises means defining threads on an external portion of said electrode mounting means; and means defining a plurality of threads on an internal portion of said hollow housing, said hollow housing threads cooperatively engageable with said electrode mounting means threads to fix said electrode mounting means in said hollow housing.

5. A detecting device according to claim 4, wherein said third holding element of said electrode mounting means includes means defining a lateral channel therein in communication with said central channel, for permitting filling of said central channel with electrolyte;

said first holding element includes:

means defining an aperture in a wall of said first holding element; and means for removably plugging said aperture in said wall of said first holding element.

6. A detecting device according to claim 3, wherein said bottom of said container of the electrode mounting means is in contact with said bottom of said hollow housing and, said means for removably fixing said electrode mounting means in said hollow housing comprises bolts extending around the periphery of said cap.

7. A detecting device according to claim 6, wherein said third holding element includes means defining a lateral channel therein in communication with said central channel for permitting filling of said central channel with electrolyte; and said cap includes:

means defining a second aperture in said cap; and means for removably plugging said second aperture in said cap.

8. A detecting device according to claim 1, 5 or 7, wherein said base further includes means for sampling said fluid adjacent said polymeric membrane.

9. A detecting device according to claim 1, 5 or 7, said device further comprising a thermistor inserted between said container and said cap of said electrode mounting means;

a multifunction converter connected to said electrodes and said thermistor for adjusting said electrical signal to compensate for fluctuations in temperature of the device.

10. A detecting device according to claim 1, 5 or 7, wherein said device further includes an insulated, thermally protected enclosure enclosing said base, said hollow housing and said electrode mounting means.

* * * * *